United States Patent
Hofen et al.

(10) Patent No.: US 6,720,436 B2
(45) Date of Patent: Apr. 13, 2004

(54) PROCESS FOR THE EPOXIDATION OF OLEFINS

(75) Inventors: Willi Hofen, Rodenbach (DE); Georg Thiele, Hanau (DE); Thomas Haas, Frankfurt (DE); Wolfgang Wöll, Maintal (DE); Percy Kampeis, Dortmund (DE); Bärbel Kolbe, Witten (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/384,217

(22) Filed: Mar. 7, 2003

(65) Prior Publication Data

US 2003/0212282 A1 Nov. 13, 2003

Related U.S. Application Data

(60) Provisional application No. 60/364,626, filed on Mar. 18, 2002.

(51) Int. Cl.$^7$ .............................................. C07D 301/12
(52) U.S. Cl. ...................................... 549/531; 549/523
(58) Field of Search .................................. 549/531, 523

(56) References Cited

U.S. PATENT DOCUMENTS

| | | |
|---|---|---|
| 2,870,171 A | 1/1959 | Gable |
| 4,410,501 A | 10/1983 | Taramasso et al. |
| 4,833,260 A | 5/1989 | Neri et al. |
| 5,523,426 A | 6/1996 | Jubin, Jr. et al. |
| 5,591,875 A | 1/1997 | Chang et al. |
| 5,599,955 A | 2/1997 | Vora et al. |
| 5,620,935 A | 4/1997 | Thiele |
| 5,675,026 A | 10/1997 | Thiele |
| 5,760,253 A | 6/1998 | Danner et al. |
| 5,849,937 A | 12/1998 | Jubin, Jr. et al. |
| 5,849,938 A | 12/1998 | Reuter et al. |
| 5,912,367 A | 6/1999 | Chang |
| 6,042,807 A | 3/2000 | Faraj |
| 6,063,941 A | 5/2000 | Gilbeau |
| 6,372,924 B2 | 4/2002 | Thiele |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 | 2/1984 |
| EP | 0 133 510 A1 | 2/1985 |
| EP | 0 230 349 | 7/1987 |
| EP | 0 230 949 | 8/1987 |
| EP | 0 425 893 A1 | 5/1991 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 1 122 248 | 8/2001 |
| EP | 1 138 387 | 10/2001 |
| EP | 1 221 442 | 7/2002 |
| JP | 2166636 | 8/1990 |
| WO | WO 97/47613 | 12/1997 |
| WO | WO 97/47614 | 12/1997 |
| WO | WO 98/47845 | 10/1998 |
| WO | WO 99/01445 | 1/1999 |
| WO | WO 99/07690 | 2/1999 |
| WO | WO 99/11639 | 3/1999 |
| WO | WO 00/07695 | 2/2000 |
| WO | WO 00/17178 | 3/2000 |
| WO | WO 00/25881 | 5/2000 |
| WO | WO 02/02545 A1 | 1/2002 |

*Primary Examiner*—Ba K. Trinh
(74) *Attorney, Agent, or Firm*—Smith, Gambrell & Russell, LLP

(57) ABSTRACT

A process for the catalytic epoxidation of olefins in at least one reaction stage comprising:
(a) reacting the olefin with hydrogen peroxide in an organic, water-miscible solvent in the presence of a titanium silicalite catalyst in a reactor while continuously feeding an inert gas stream into the reactor,
(b) continuously removing an exit gas stream containing olefin oxide, unreacted olefin, oxygen and inert gas from the reactor,
(c) bringing the exit gas stream into contact in an absorption unit with the same solvent as used in the reaction stage,
(d) removing a solvent stream loaded with olefin and olefin oxide from the absorption unit and
(e) discharging an gas stream containing oxygen and the inert gas from the absorption unit.

26 Claims, 1 Drawing Sheet

PROCESS FOR THE EPOXIDATION OF OLEFINS

REFERENCE TO A RELATED APPLICATION

This application claims the benefit of our provisional application No. 60/364,626 filed Mar. 18, 2002 which is relied on and incorporated herein by reference.

INTRODUCTION AND BACKGROUND

The present invention relates to a process for the epoxidation of olefins, whereby measures are taken to ensure safe operation of the process in all stages without compromising the overall economics of the process.

It is known from EP-A 100 118 that propene can be reacted with hydrogen peroxide to yield propene oxide if titanium silicalite is used as the catalyst. A secondary reaction which always occurs to a slight extent on the titanium silicalite catalyst is the decomposition of hydrogen peroxide to form molecular oxygen. It is known from EP-A 659 473 to introduce a small amount of propene vapor into the reactor for purposes of purging any oxygen formed by hydrogen peroxide decomposition. A purge stream comprising predominantly propene and some oxygen and propene oxide is removed from the reactor.

EP-A 936 219 and EP-A 1 074 547 describe a process for regeneration of a titanium silicalite catalyst that has been deactivated in a process of epoxidation of propylene with hydrogen peroxide. In that process the reactor is discontinuously purged with an inert gas to remove propane since the regeneration of the catalyst has to be performed in the absence of the olefin. It is discussed in these references that the purging has the additional advantage that oxygen formed by the decomposition of hydrogen peroxide is also periodically removed from the reactor, thereby improving the safety of the process. But to ensure safe operation inert gas purging has to be conducted in short intervals which leads to undesired long shut-down periods.

EP-A 1 085 017 and WO 99/48883 disclose, with regard to some preferred embodiments of a process for epoxidation of propylene with hydrogen peroxide, the possibility of introducing a gas stream comprising propene and inert gas into the reactor. But there is no discussion with respect to oxygen decomposition or safety requirements.

All the prior described processes as discussed above do, however, suffer the disadvantage in common that considerable quantities of propene and propene oxide are lost together with the oxygen in the purge stream.

EP-A 719 768 and EP-A 1 122 246 describe a process for epoxidation of olefins preferably propene with hydrogen peroxide whereby a vapor stream comprising propene, propene oxide and oxygen leaving the reactor is treated in an absorption unit to recover valuable products from the vapor stream. Due to the increase of the oxygen concentration in the gas room of the absorption unit because the gas is depleted of propene and propene oxide it may be advantageous for safety reasons to introduce an inert gas stream into the absorption unit. Although these prior art documents deal with safety aspects in the absorption unit they do not address safety requirements of the entire process. Especially in the epoxidation reactor itself no measures are taken to ensure safe conduct of the process. Consequently the process can only be conducted within a narrow range of process parameters to ensure safety of the reaction with the result that there is a high risk associated with any kind of malfunction in the reaction stage.

An object of the present invention is accordingly to provide a process for the epoxidation of olefins having an improved balance of operation safety and economics of the process.

SUMMARY OF THE INVENTION

The above and other objects of the invention can be achieved by a process for the catalytic epoxidation of olefins in at least one reaction stage comprising:

(a) reacting the olefin with hydrogen peroxide in an organic, water-miscible solvent in the presence of a titanium silicalite catalyst in a reactor while continuously feeding an inert gas stream into the reactor;

(b) continuously removing an exit gas stream containing olefin oxide, unreacted olefin, oxygen and inert gas from the reactor;

(c) bringing the exit gas stream into contact in an absorption unit with the same solvent as used in the reaction stage;

(d) removing a solvent stream loaded with olefin and olefin oxide from the absorption unit; and (e) discharging an gas stream containing oxygen and the inert gas from the absorption unit.

BRIEF DESCRIPTION OF DRAWING

The present invention will be further understood with reference to the accompanying drawing which substantially represents a flow diagram of the process of this invention.

DETAILED DESCRIPTION OF THE INVENTION

Figure 1:
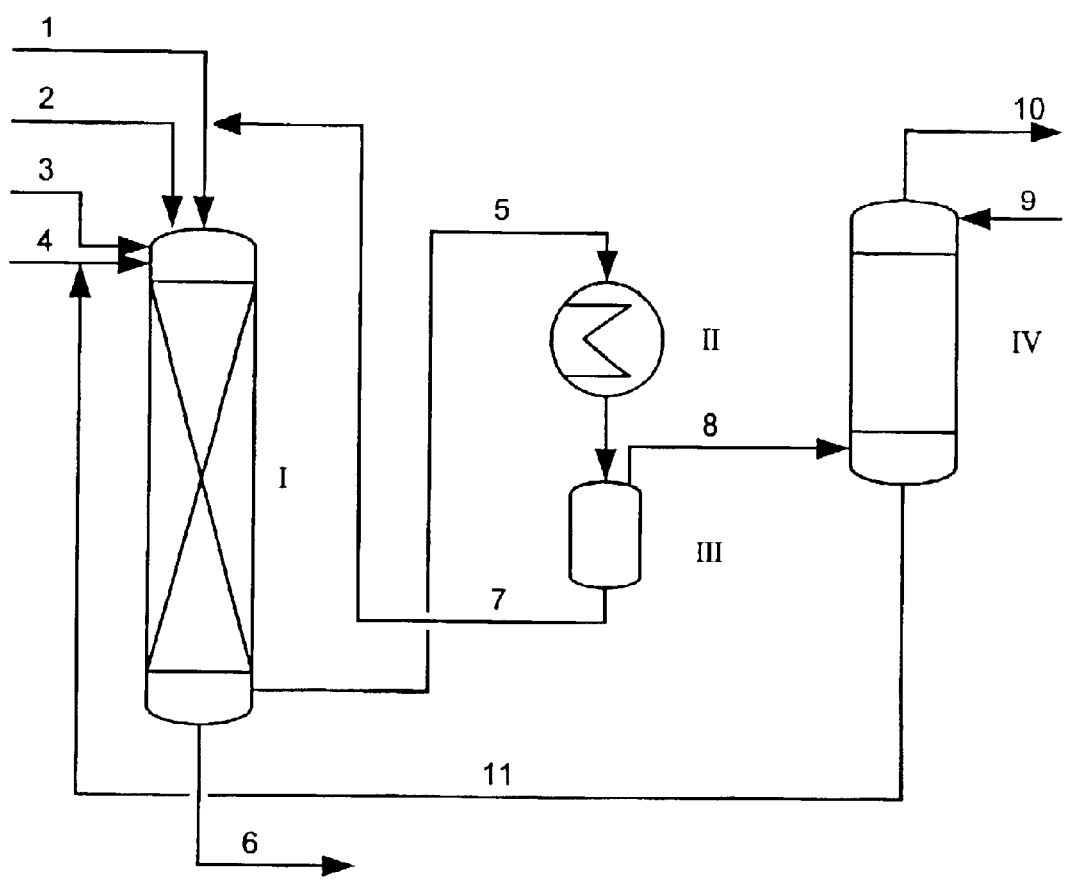

It has now been found that not only can the losses of olefin and olefin oxide be reduced which occur on discharge of the exit gas stream containing oxygen during the epoxidation of olefin with hydrogen peroxide and a titanium silicalite catalyst, in a simple manner by absorbing the majority of the olefin oxide, olefin and optionally the corresponding alkane with the solvent used for the epoxidation, but also the safety of the entire epoxidation process in all stages can be ensured. A particular advantage of the present invention is that the epoxidation process can be conducted within a wide range of process parameters without compromising safety of the process since due to the inert gas stream present in the reactor it is always ensured that, despite the decomposition of hydrogen peroxide, an ignitable composition will not be formed. Thus the process of the invention can be more easily adapted to changing requirements and even in case of malfunction during the conduct of the process, like interruption of the olefin supply, formation of ignitable compositions can be avoided. A further advantage is, that there is no longer any necessity for introduction of inert gas into the absorption unit.

According to a preferred embodiment of the present invention, the inert gas stream is introduced near the reactor inlet and the exit gas stream is removed near the reactor outlet. It is preferred that no inert gas be additionally introduced into the absorption unit.

According to a particularly preferred embodiment of the present invention the exit gas stream after leaving the reactor and prior to entering the absorption unit is directed through an condensation unit wherein condensable components of the exit gas stream like olefin, olefin oxide, the alkane corresponding to the olefin as well as the solvent used in the epoxidation reaction are partially condensed. It is advantageous to maintain approximately the same pressure in the condensation unit as in the reactor. The pressure in the condensation unit is at least 50%, preferably at least 75%, more preferably at least 90%, of the pressure in the epoxidation stage and most preferably about the same pressure as in the epoxidation stage. By adjusting the pressure within the condensation unit as high as possible a large portion of the condensable material can be removed form the exit gas stream with simple low energy measures, such as coolers run with cooling water. Other suitable apparatus for the condensation unit are any apparatus that can be used as heat exchanger such as shell and tube heat exchangers and plate-type heat exchangers.

The condensate separated from the exit gas stream can be combined with the liquid reaction mixture removed from the reactor and processed in subsequent working-up stages. Alternatively the condensate can be recycled to the reactor. In a preferred embodiment, if propene is used as the olefin the condensate predominantly comprises organic solvent and propene and is recycled to the reaction stage. In case propene comprising propane is used as starting material, it may be advantageous to subject at least a part of the condensate to a separation operation whereby propane is removed prior to recycling the condensate to avoid an unwanted build-up of propane in the reaction stage.

An important advantage of having a condensation unit between reactor and absorption unit is that the load of valuable components in the exit gas stream is already considerably reduced prior to entering the absorption unit. Consequently the amount of solvent necessary in the absorption unit that has to be recycled within the process and the volume of the absorption unit can be considerable reduced. Thereby process costs as well as investment costs can be reduced contributing to the overall economical improvements associated with the present invention.

Most importantly a safe operation of the condensation unit within wide ranges of process parameters is only possible if inert gas is introduced into the epoxidation reactor and is thus present in the exit gas stream processed in the condensation unit. In the condensation unit the content of condensable organic components in the exit gas stream is reduced. Thus the concentration of oxygen in the gas phase is increased with the possibility that an ignitable gas composition is formed. Thus even if the process parameters were carefully controlled and/or only a small amount of condensable components were removed, thereby compromising the above discussed economical advantages, there would be still a considerable high risk of formation of an ignitable composition if no inert gas was introduced into the reactor. Thus the present invention is especially advantageous if a condensation unit is used in the work up of the exit gas stream leaving the epoxidation reactor.

The quantity of inert gas introduced into the reactor is preferably selected as a function of the quantity and composition of the exit gas stream leaving the reaction stage such that the oxygen concentration in the exit gas stream at any stage of the work up of the exit gas is low enough to avoid the formation of an ignitable composition. Furthermore, preferably the amount of inert gas is selected such that not more than 5%, preferably not more than 2% of the total propene oxide generated in the reactor is removed with the exit gas stream. Thus, even in the case of variation in product streams in the overall process, it is very simple to constantly maintain the composition of the gas phase at any stage of the work up of the exit gas such that an ignitable mixture cannot occur. As a result, the dimensions of the absorption unit and the amount of the absorbing solvent can be small while ensuring safety of the entire process.

In a particularly preferred embodiment of the present invention the oxygen concentration in the exit gas stream leaving the reactor is measured, whereby in the embodiment using a condensation unit the oxygen concentration of the exit gas stream is measured after leaving the condensation unit. The amount of inert gas introduced into the reactor and/or the amount of exit gas leaving the reactor is controlled by measuring the oxygen content in the exit gas stream as explained above to maintain oxygen concentration in the exit gas stream constant. Most preferably, the amount of the exit gas stream leaving the reactor is controlled by measuring the oxygen content as explained above, whereby the ratio of inert gas stream introduced into the reactor and exit gas stream removed from the reactor is held constant.

Thus an improved balance of safety requirements and economics of the overall epoxidation process is achieved by the present invention.

Suitable inert gases are any gases which dissolve only slightly in the solvent used for epoxidation, do not react with hydrogen peroxide and olefin oxide under the epoxidation reaction conditions and do not form explosive mixtures with oxygen. The inert gas preferably used comprises nitrogen, an inert gas obtained by combustion of a methane-air mixture, water vapor, carbon dioxide or mixtures thereof.

Suitable solvents are any solvents which are not oxidized or are only slightly oxidized by hydrogen peroxide under the selected reaction conditions and dissolve in water in a quantity of greater than 10 wt. %. Preferred solvents are those which are unlimitedly miscible with water. Suitable solvents are alcohols, such as for example methanol, ethanol or tert.-butanol; glycols, such as for example ethylene glycol, 1,2-propanediol or 1,3-propanediol; cyclic ethers, such as for example tetrahydrofuran, dioxane or propene oxide; glycol ethers, such as for example ethylene glycol monomethyl ether, ethylene glycol monoethyl ether, ethylene glycol monobutyl ether or propylene glycol monomethyl ethers and ketones, such as for example acetone or 2-butanone. Methanol is particularly preferably used as the solvent. Absorption is performed at a total pressure in the range from 1 to 25 bar, preferably at the same pressure as the epoxidation reaction, at which the exit gas containing oxygen is obtained. Absorption may be performed at temperatures between the melting point of the solvent and 100° C., preferably in the range from 0 to 60° C.

In a particularly preferred embodiment of the present invention, the exit gas stream is passed countercurrently to the solvent. An absorption unit which is suitable for this embodiment is in particular a column with an inert packing or inserts, wherein the exit gas stream loaded inter alia with olefin, olefin oxide and the inert gas are fed into the bottom of the column, the solvent is supplied to the top of the column, the exit gas stream is discharged at the top of the column and the solvent stream loaded with olefin and olefin oxide is drawn off from the bottom of the column.

According to an alternative embodiment of the present invention in the absorption unit the gas phase is dispersed in a continuous liquid phase of the solvent.

The advantage of said embodiment is that if the gas phase comprising combustible components and oxygen is dispersed in a continuous liquid phase of the solvent during absorption, even if due to the depletion of combustible components from the gas phase the oxygen concentration in the gas phase rises above the explosion limit, the gas phase still cannot be ignited within the absorption unit because the gas phase is finely dispersed in the continuous liquid phase of the solvent. Consequently, the amount of inert gas introduced into the reactor can be reduced and control of oxygen concentration is only necessary to the extent that the exit gas stream may not become an ignitable composition prior to entering the absorption unit. Thereby safety of the process is ensured since the gas phase, although the oxygen content thereof may be above the explosion limit, cannot be ignited.

In this way, the absorption process is very efficient since the gas phase contains less inert gas. Consequently, the dimensions of the absorption unit can be further reduced, thereby saving investment costs, and a reduced volume of the absorption fluid; i.e. the solvent, can be used, with the result that the amount of solvent to be recycled or processed in working-up stages can be considerably reduced, thereby improving the overall economics of the process.

According to a preferred embodiment, the gas bubbles dispersed in the continuous phase of the absorption solvent have a diameter of 10 millimeters or less, preferably 2–10 millimeters, most preferred 5 millimeters at most.

According to a specifically preferred embodiment of the present invention, the gas stream is introduced into the absorption unit at a lower section of the absorption unit, and the liquid solvent phase enters the absorption unit at a position upwards with respect to the location where the gas stream enters the absorption unit, and the liquid solvent phase exits the absorption unit at a position below the entry of the gas stream into the absorption unit. As a result, it is achieved that the gas stream and the solvent pass through the absorption unit in a countercurrent manner. Preferably, the absorption unit is run as bubble column.

The flow rate of the dispersed gas phase and of the continuous liquid solvent phase can be varied in wide ranges as long as the requirement that the liquid phase is continuous and the gas phase is dispersed is maintained. The flow rate per cross-section for the gas phase is preferably 10–100 $m^3/m^2h$, more preferred 20–60 $m^3/m^2h$ and the flow rate per cross-section for the liquid phase is preferably 50–200 $m^3/m^2h$, more preferred 100–150 $m^3/m^2h$.

According to a preferred embodiment of the present invention, the exit gas stream is introduced into the absorption unit with a system of ring nozzles to finely disperse the gas phase in the continuous liquid phase. The dimensions of the absorption unit as well as the flow conditions of the gas phase and the continuous solvent phase are selected to provide gas bubbles dispersed in the continuous liquid phase having a diameter of 10 millimeters or less, preferably 2–10 millimeters, more preferred 5 millimeters at most. Several measures can be taken singly or in combination to control the above defined bubbles size. For example, the cross-section of the orifices of the ring nozzles can be selected to be within the range of 0.2–2 mm, and/or sieve trays can be positioned within the absorption unit in defined spacing having an orifice cross-section of 0.2–2 mm and/or the flow rate of the liquid phase and the gas phase are adjusted as defined above. If sieve tray are used the ratio of the free cross-section of the sieve trays to the cross-section of the absorption unit is preferably adjusted to ensure a flow rate of the gas phase through the perforated plates of 0.5–2 m/s.

The absorption unit that can be used in the above described preferred embodiment of the present invention may comprise heat exchange means and/or gas dispersing means. Heat exchange means can be useful to control the temperature in the absorption unit, especially to remove the heat of absorption. Gas dispersing means can be present to improve gas dispersion and the mass transfer between gas phase and continuous solvent phase. Preferably sieve trays and particularly preferably sieve trays with downcorners are used as gas dispersing means.

For safety reasons, it is preferred in this embodiment to introduce inert gas into the headspace above the liquid level within the absorption unit. In that way, the gas stream exiting the liquid solvent phase is diluted to the extent that the oxygen concentration is below the explosion limit. Since the gas phase after exiting the liquid solvent phase is no longer finely dispersed, the gas mixture will become ignitable in case the oxygen concentration due to depletion of combustible components during the absorption is above the explosion limit. Here the same inert gas can be used as introduced into the reactor.

According to an alternative embodiment, the volume of the headspace in the absorption unit above the liquid level is reduced by displacers and the absorption unit is equipped with pressure release means and a flame barrier in the gas exit line. In that case, the amount of inert gas introduced into the headspace can be considerably reduced while ensuring sufficient safety for the absorption process.

The solvent stream loaded with olefin and olefin oxide recovered from the absorption unit is either returned to the reaction stage or is passed to a working up stage downstream from the reaction stage. Preferably the liquid product stream from the reaction stage is worked up and the recovered solvent so obtained is returned in part to the absorption unit and in part to the reaction stage.

The process according to the invention is suitable for the epoxidation of olefins having 2 to 6 carbon atoms. The epoxidation of propene to yield propene oxide is most highly preferred.

Crystalline, titanium-containing zeolites of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501 which is relied on and incorporated herein for that purpose. The titanium silicalite catalyst may be employed as a powder or as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Granules corresponding to EP-A 893 158 are preferably used as suspension catalysts. Extrudates with a diameter of 1 to 5 mm are preferably used as fixed bed catalysts.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilized solutions. Also suitable are unstabilized, aqueous hydrogen peroxide solutions such as are obtained in the anthraquinone process for producing hydrogen peroxide. Alternatively, hydrogen peroxide solutions in alcohols, preferably in methanol can be used. These alcoholic solutions can be prepared be reaction of hydrogen and oxygen in presence of a noble metal catalyst and the alcohol.

The epoxidation of olefins, preferably propene, is carried out at a temperature of −10° to 100° C., preferably at 20° to 70° C. The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 10. When adding a solvent the amount of solvent is preferably chosen so that only a liquid phase is present in the reaction mixture. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

In a preferred embodiment of the process according to the invention propene is used that may contain between 0% and 15% of propane. Propene may be fed as a liquid as well as in gaseous form into the reaction system. The amount of propene that is fed in is chosen so that under the reaction conditions in the reactors a gas phase is formed consisting predominantly of propene, and so that from the first reactor of the reaction system a waste gas can be removed whose oxygen content lies outside the explosion limits for propylene-oxygen mixtures.

The pressure in the reactor is preferably from atmospheric pressure to 50 bar. In case of epoxidation of propene the pressure in the reaction system is preferably chosen to be between 50% and 100% of the saturated vapour pressure of propylene at the reaction temperature.

The invention will now be discussed in more detail referring to a preferred embodiment according to FIG. 1.

FIG. 1 exhibits a schematic presentation of a preferred embodiment of the present invention.

Referring to FIG. 1, propene 1, inert gas 2, hydrogen peroxide 3 and methanol 4 are continuously fed into the epoxidation reactor I containing an epoxidation catalyst. A liquid reaction mixture is continuously removed as product stream 6 from the reactor I and is directed to subsequent working-up stages that are not shown in FIG. 1. Additionally an exit gas stream 5 is continuously removed from the reactor I and directed to a condensation unit II, where the condensable components of the exit gas stream 5 are partially condensed. The resulting two phase mixture is directed into a phase separator III wherein the liquid phase 7 comprising the condensed components of the exit gas stream 5 is separated from the gas phase 8. The liquid phase 7 is recycled to the reactor I and the gas phase 8 is fed to the absorption unit IV. The gas phase 8 is directed through the absorption unit IV counter-currently to a methanol stream 9. A gas stream 10 substantially free of any valuable products is removed from the absorption unit IV and a solvent phase 11 loaded with propene oxide and propene is recycled to the reactor I.

The present invention refers to a process for the catalytic epoxidation of olefins in at least one reaction stage comprising:
(a) reacting the olefin with hydrogen peroxide in an organic, water-miscible solvent in the presence of a titanium silicalite catalyst in a reactor while continuously feeding an inert gas stream into the reactor,
(b) continuously removing an exit gas stream containing olefin oxide, unreacted olefin, oxygen and inert gas from the reactor,
(c) bringing the exit gas stream into contact in an absorption unit with the same solvent as used in the reaction stage,
(d) removing a solvent stream loaded with olefin and olefin oxide from the absorption unit and
(e) discharging an gas stream containing oxygen and the inert gas from the absorption unit.

Preferably no inert gas is additionally introduced into the absorption unit.

Preferably the quantity of inert gas introduced is selected as a function of the quantity and composition of the exit gas stream leaving the reaction stage such that the exit gas stream is no longer of an ignitable composition and such that not more than 5%, preferably not more than 2% of the total propene oxide generated in the reactor is removed with the exit gas stream.

The inert gas is selected from a gas which dissolves only slightly in the solvent used for epoxidation, does not react with hydrogen peroxide and olefin oxide under the epoxidation reaction conditions and does not form explosive mixtures with oxygen, preferably from nitrogen, an inert gas obtained by combustion of a methane-air mixture, water vapor, carbon dioxide or mixtures thereof.

Preferably the inert gas stream is introduced near the reactor inlet and the exit gas stream is removed near the reactor outlet.

Preferably the reactor is a trickle-bed reactor and the inert gas is introduced into the reactor above the trickle-bed and the exit gas stream is removed below the trickle-bed.

Preferably the process according to the present invention is characterized in that from the exit gas stream part of the olefin oxide, the unreacted olefin and the solvent is removed by partial condensation prior to introducing the exit gas stream into the absorption unit.

Preferably the absorption unit is a column with an inert packing or inserts and the gas streams are fed into the bottom of the column, the solvent is supplied to the top of the column as solvent stream, the exit gas stream is discharged at the top of the column and the solvent stream loaded with olefin and olefin oxide is drawn off from the bottom of the column.

Preferably the process according to according to the present invention is characterized in that during the absorption the gas phase is dispersed in a continuous liquid phase of the solvent.

Preferably the gas bubbles dispersed in the continuous phase have a diameter of 10 mm or less, preferably of 5 mm at the most.

Preferably the gas stream is introduced into an absorption unit at a lower section of the absorption unit and the liquid solvent phase enters the absorption unit at a position upwards with respect to the location the gas stream enters the absorption unit, whereby the gas stream and the solvent pass through the absorption unit counter-currently and the liquid solvent phase exits the absorption unit at a position below the entry of the gas stream into the absorption unit.

Preferably the absorption unit is run as bubble column.

Preferably the gas stream is introduced into the absorption unit through a system of ring nozzles.

Preferably the flow conditions within the absorption unit are selected to provide gas bubbles dispersed in the continuous liquid phase having a diameter of 10 mm or less, preferably of 5 mm at the most.

Preferably the absorption unit comprises heat exchange means and/or gas dispersing means.

Preferably sieve trays are positioned within the absorption unit.

Preferably the solvent stream loaded with olefin and olefin oxide is either returned to the reaction stage or is passed to a working up stage downstream from the reaction stage.

Preferably the liquid product stream from the reaction stage is worked up and the recovered solvent so obtained is returned in part to the absorption unit and in part to the reaction stage.

Preferably the olefin is an olefin having 2–6 carbon atoms, more preferably propene.

Preferably the solvent is selected from among alcohols, glycols, cyclic ethers, glycol ethers and ketones and is preferably methanol.

Further variations and modifications will be apparent to those skilled in the art from the foregoing and are intended to be encompassed by the claims appended hereto.

We claim:

1. A process for the catalytic epoxidation of olefins in at least one reaction stage comprising:
   (a) reacting the olefin with hydrogen peroxide in an organic, water-miscible solvent in the presence of a titanium silicalite catalyst in a reactor while continuously feeding an inert gas stream into the reactor,
   (b) continuously removing an exit gas stream containing olefin oxide, unreacted olefin, oxygen and inert gas from the reactor,
   (c) bringing the exit gas stream into contact in an absorption unit with the same solvent as used in the reaction stage,
   (d) removing a solvent stream loaded with olefin and olefin oxide from the absorption unit and
   (e) discharging a gas stream containing oxygen and the inert gas from the absorption unit.

2. The process of claim 1, wherein no inert gas is additionally introduced into the absorption unit.

3. The process of claim 1, wherein the quantity of inert gas introduced is selected as a function of the quantity and composition of the exit gas stream leaving the reactor such that the exit gas stream is no longer of an ignitable composition and such that not more than 5% of the total propene oxide generated in the reactor is removed with the exit gas stream.

4. The process of claim 3, wherein not more than 2% of the total propene oxide generated in the reactor is removed with the exit gas stream.

5. The process of claim 1, wherein the inert gas is a gas which dissolves only slightly in the solvent used for epoxidation, does not react with hydrogen peroxide and olefin oxide under the epoxidation reaction conditions and does not form explosive mixtures with oxygen.

6. The process of claim 1, wherein the inert gas is selected from nitrogen, an inert gas obtained by combustion of a methane-air mixture, water vapor, carbon dioxide or mixtures thereof.

7. The process of claim 1, wherein the inert gas stream is introduced near the reactor inlet and the exit gas stream is removed near the reactor outlet.

8. The process of claim 7, wherein the reactor is a trickle-bed reactor and the inert gas is introduced into the reactor above the trickle-bed and the exit gas stream is removed below the trickle-bed.

9. The process of claim 1, wherein a part of the olefin oxide, the unreacted olefin and the solvent is removed from the exit gas stream by partial condensation prior to introducing the exit gas stream into the absorption unit.

10. The process of claim 1, wherein the absorption unit is a column with an inert packing or inserts and the exit gas stream is fed to the bottom of the column, the solvent is supplied to the top of the column, a gas stream containing oxygen and the inert gas is discharged from the top of the column and the solvent stream loaded with olefin and olefin oxide is withdrawn from the bottom of the column.

11. The process of claim 1, wherein in the absorption unit the exit gas stream is dispersed in a continuous liquid phase of the solvent.

12. The process of claim 11, wherein the gas bubbles formed by dispersing the exit gas stream in the continuous liquid phase have a diameter of 10 mm or less.

13. The process of claim 11, wherein the gas bubbles formed by dispersing the exit gas stream in the continuous liquid phase have a diameter of 5 mm or less.

14. The process of claim 11, wherein the exit gas stream is introduced into the absorption unit at a lower section of the absorption unit and the liquid solvent phase enters the absorption unit at a position above the point where the exit gas stream enters the absorption unit, whereby the gas stream and the solvent pass through the absorption unit counter-currently and the solvent stream loaded with olefin and olefin oxide leaves the absorption unit at a position below the entry of the exit gas stream into the absorption unit.

15. The process of claim 11, wherein the absorption unit comprises heat exchange means and/or gas dispersing means.

16. The process of claim 15, wherein the gas dispersing means comprise a system of ring nozzles.

17. The process of claim 15, wherein sieve trays are positioned as gas dispersing means within the absorption unit.

18. The process of claim 11, wherein the absorption unit is operated as a bubble column.

19. The process of claim 18, wherein the flow conditions within the absorption unit are selected to provide gas bubbles dispersed in the continuous liquid phase having a diameter of 10 mm or less.

20. The process of claim 18, wherein the flow conditions within the absorption unit are selected to provide gas bubbles dispersed in the continuous liquid phase having a diameter of 5 mm or less.

21. The process of claim 1, wherein the solvent stream loaded with olefin and olefin oxide is either returned to the reactor or is passed to a working up stage downstream from the reactor.

22. The process of claim 1, wherein a liquid product stream withdrawn from the reactor is worked up and the thereby recovered solvent is used in part as solvent in the absorption unit and returned in part to the reaction stage.

23. The process of 1, wherein the olefin is an olefin having 2 to 6 carbon atoms.

24. The process of claim 23, wherein the olefin is propene.

25. The process of claim 1, wherein the solvent is selected from among alcohols, glycols, cyclic ethers, glycol ethers and ketones.

26. The process of claim 25, wherein the solvent is methanol.

* * * * *

UNITED STATES PATENT AND TRADEMARK OFFICE
CERTIFICATE OF CORRECTION

PATENT NO. : 6,720,436 B2
DATED : April 13, 2004
INVENTOR(S) : Hofen, Willi et al.

It is certified that error appears in the above-identified patent and that said Letters Patent is hereby corrected as shown below:

Title page,
Item [75], Inventors, should read as follows:
-- [75] Inventors: Willi Hofen, Rodenbach (DE); Georg Thiele, Hanau (DE); Thomas Haas, Frankfurt (DE); Percy Kampeis, St. Wendel (DE); Bärbel Kolbe, Witten (DE) --

Column 10,
Line 49, claim 23 should read as follows:
23. The process of claim 1, wherein the olefin is an olefin having 2 to 6 carbon atoms.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,720,436 B2
DATED : April 13, 2004
INVENTOR(S) : Hofen, Willi et al.

It is certified that error appears in the above-identified patent and that said Letters Patent is hereby corrected as shown below:

Title page,
Item [75], Inventors, should read as follows:
-- [75] Inventors: Willi Hofen, Rodenbach (DE); Georg Thiele, Hanau (DE); Thomas Haas, Frankfurt (DE); Wolfgang Wöll, Maintal (DE); Percy Kampeis, St. Wendel (DE); Bärbel Kolbe, Witten (DE) --

Column 10,
Line 49, claim 23 should read as follows:
23. The process of claim 1, wherein the olefin is an olefin having 2 to 6 carbon atoms.

This certificate supersedes Certificate of Correction issued November 23, 2004.

Signed and Sealed this

Twenty-eighth Day of February, 2006

JON W. DUDAS
*Director of the United States Patent and Trademark Office*